United States Patent [19]

Parker

[11] Patent Number: 5,562,698
[45] Date of Patent: Oct. 8, 1996

[54] INTRAVASCULAR TREATMENT SYSTEM

[75] Inventor: Fred T. Parker, Unionville, Ind.

[73] Assignee: Cook Incorporated, Bloomington, Ind.

[21] Appl. No.: 335,982

[22] Filed: Nov. 8, 1994

Related U.S. Application Data

[62] Division of Ser. No. 208,766, Mar. 9, 1994, Pat. No. 5,417,708.

[51] Int. Cl.$^6$ .............................................. A61M 29/00
[52] U.S. Cl. ........................ 606/200; 623/1; 128/899; 606/198
[58] Field of Search .................................. 606/108, 191, 606/192, 194, 195, 198, 200; 128/898, 899; 623/1, 11, 12

[56] References Cited

U.S. PATENT DOCUMENTS

| | | | |
|---|---|---|---|
| 3,834,394 | 9/1974 | Hunter et al. | 128/325 |
| 4,494,531 | 1/1985 | Gianturco | 606/200 |
| 4,957,501 | 9/1990 | Lahille et al. | 606/200 |
| 4,994,069 | 2/1991 | Ritchart et al. | 606/191 |
| 5,108,407 | 4/1992 | Geremia et al. | 606/108 |
| 5,108,420 | 4/1992 | Marks | 606/213 |
| 5,122,136 | 6/1992 | Guglielmi et al. | 606/32 |
| 5,133,731 | 7/1992 | Butler et al. | 606/191 |
| 5,217,484 | 6/1993 | Marks | 606/200 |
| 5,250,071 | 10/1993 | Palermo | 606/198 |
| 5,250,076 | 10/1993 | Palermo | 606/198 |
| 5,261,916 | 11/1993 | Engleson | 606/108 |

Primary Examiner—Michael Powell Buiz
Assistant Examiner—William Lewis
Attorney, Agent, or Firm—Richard J. Godlewski

[57] ABSTRACT

A percutaneous release mechanism (57) for use with an intravascular treatment device (11) in an intravascular treatment system (10). The release mechanism includes an inner member (17) having a connection mechanism (18) positioned about the distal end (14) thereof for interconnection with another connection mechanism (12) positioned on an intravascular treatment device. The release mechanism also includes an outer member tube (13) of which the inner member is positioned therein. The first and second connection mechanisms are interconnectable and positionable in the passage (16) of the tube for delivering the treatment device in a delivery state to the treatment site. The release mechanism also includes a handle (37) having parts (38, 39) connected to the inner member and outer tube, whereby movement of the proximal end of the inner member is translated to the distal end thereof for extending the interconnected connection mechanisms from the passage of the outer member tube and positioning the treatment device in a treatment state. The intravascular treatment system includes the percutaneous release mechanism along with the intravascular treatment device. The treatment device includes an occlusion coil (23) and a rigid tube (36) connected to the flexible outer member tube (35) for maintaining the delivery coil in a delivery state. In another example, the treatment device includes a blood clot filter (40) in which the percutaneous delivery mechanism is adapted for connection thereto.

18 Claims, 4 Drawing Sheets

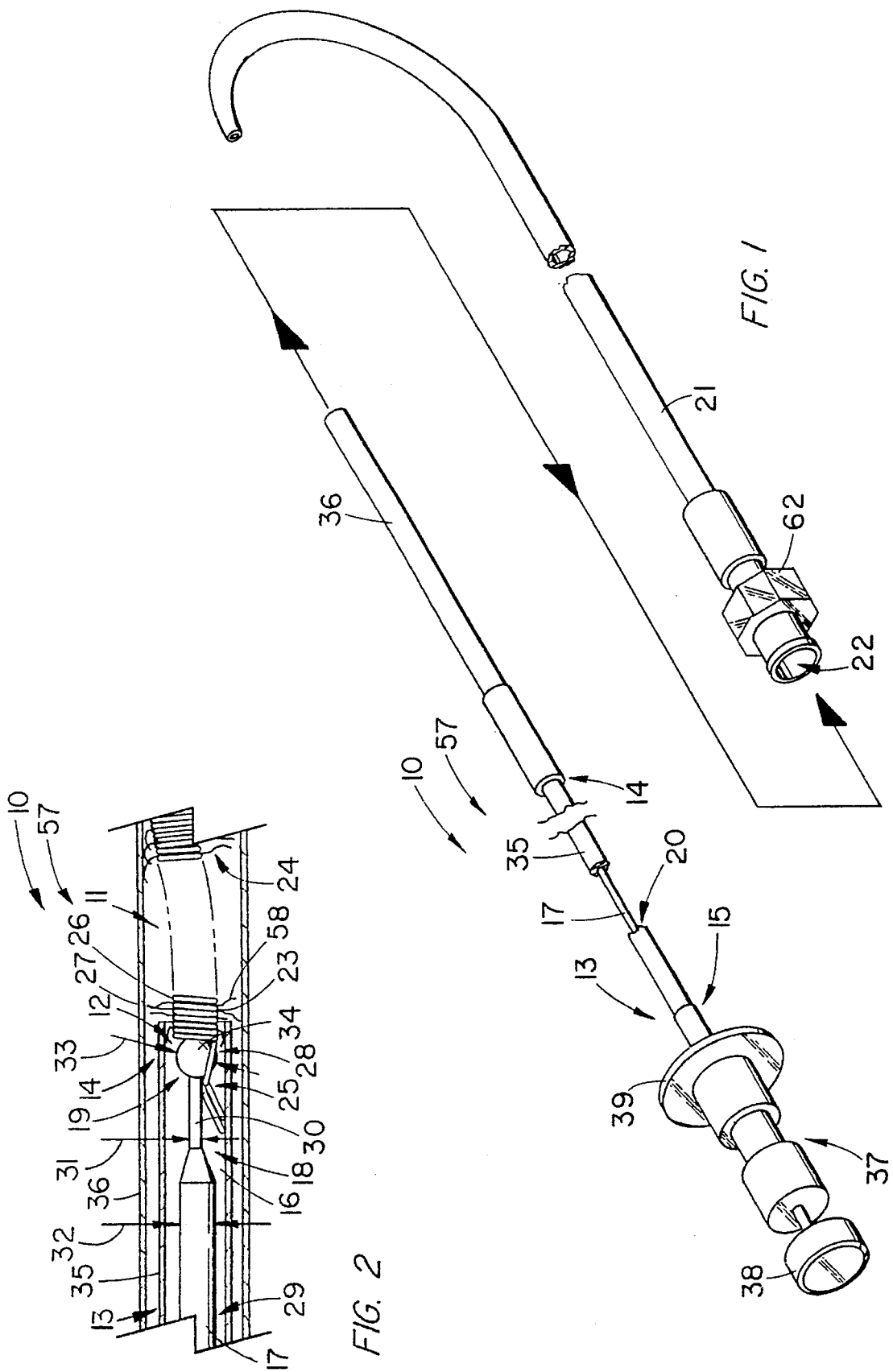

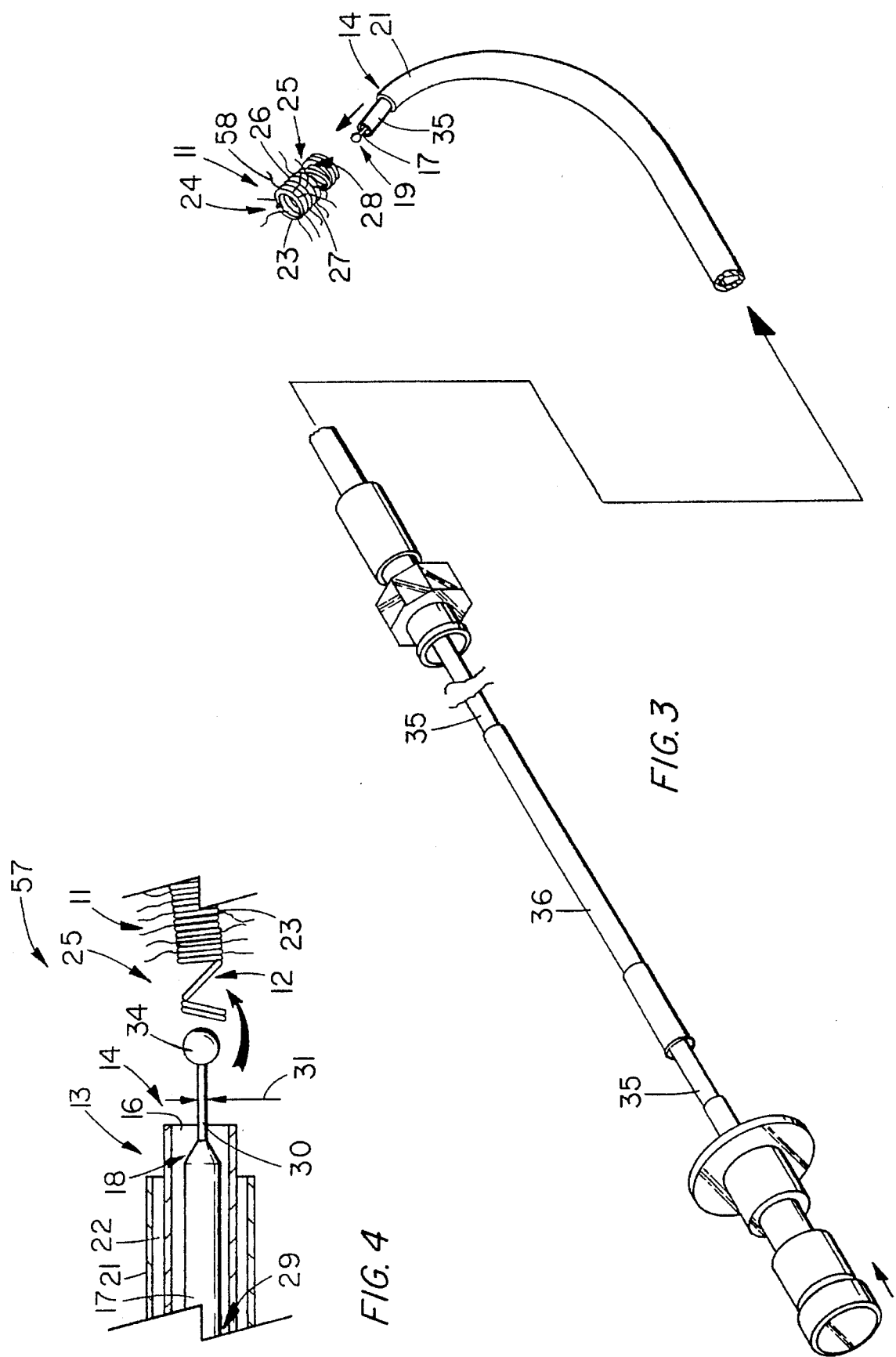

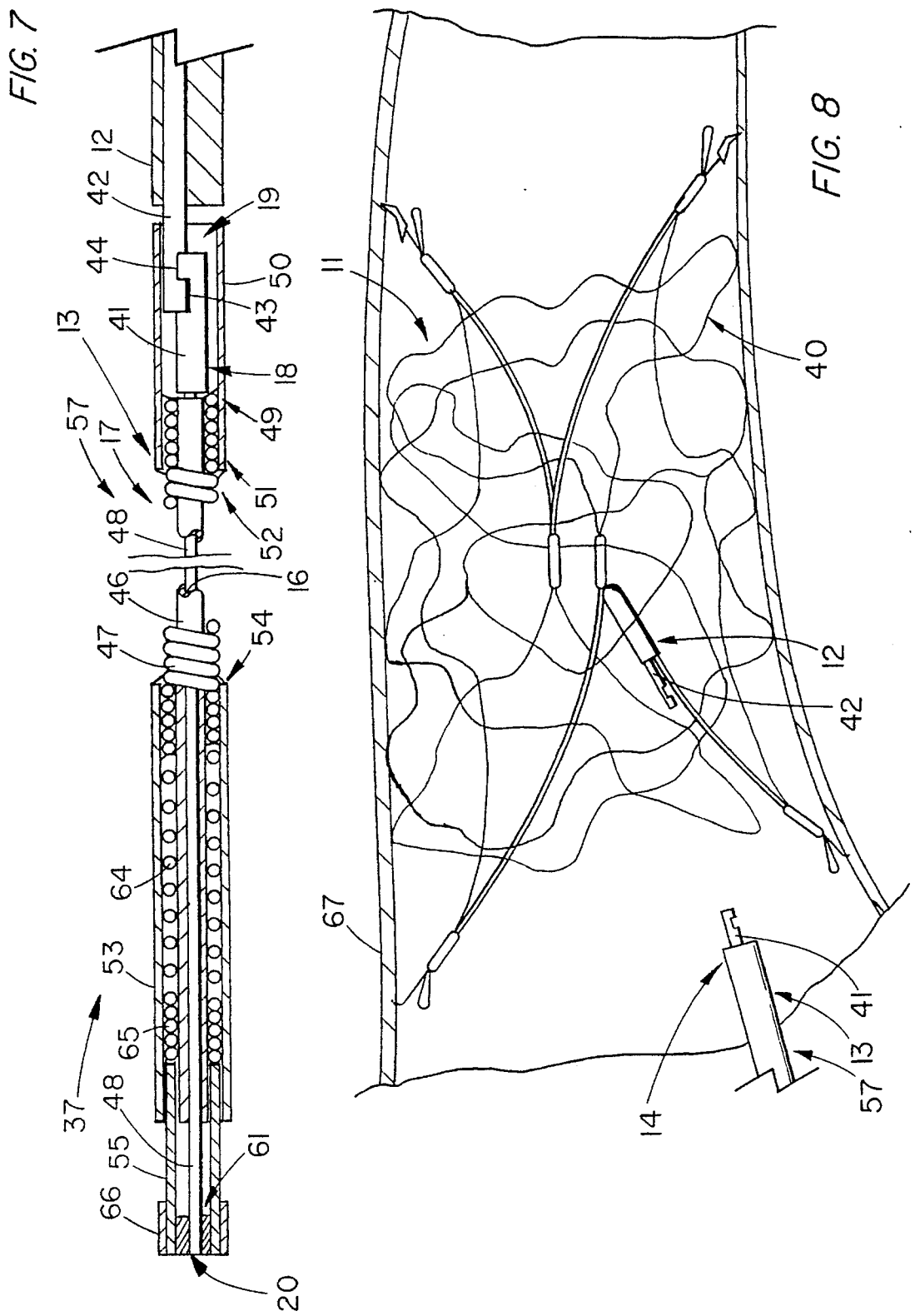

5,562,698

INTRAVASCULAR TREATMENT SYSTEM

CROSS-REFERENCE TO RELATED APPLICATIONS

This application is a divisional of patent application Ser. No. 08/208,766, filed Mar. 9, 1994, and entitled "An Intravascular Treatment System and Percutaneous Release Mechanism Therefor" now Pat. No. 5,417,708.

TECHNICAL FIELD

This invention relates generally to intravascular treatment devices and, in particular, to an intravascular treatment system for positioning a treatment device in the vascular system of a patient.

BACKGROUND OF THE INVENTION

Intravascular interventional procedures for providing an artificial embolism are desirable in some patients for controlling internal bleeding, preventing blood supply to tumors, or relieving pressure in the vessel wall near an aneurysm. Several approaches are proposed for providing an artificial embolism, including the use of an inflatable, detachable balloon or the injection of a coagulative substance. Another approach utilizes an occlusive wire coil and delivery system for positioning the coil in a desirable site of a blood vessel.

One wire coil and delivery system includes a flexible, coiled wire that when released from the distal end of a catheter assumes a randomly coiled, space-filling mass. The wire is released from the catheter by a pusher catheter with a closed distal end for engaging the proximal end of the coil. A problem with this system is that the wire coil is pushed toward the target embolism site and then assumes a randomly coiled configuration. As a result, the desirable position of the coil is targeted and aimed for but not positively attainable. Only after the coil has assumed a randomly coiled configuration can the coil be checked for desirable positioning via a visualization means such as fluoroscopy.

Another wire coil and delivery assembly includes embolic coils that are attached to the connector of a probe assembly by a heat releasable adhesive bond. To release an embolic coil, laser energy is transmitted through the probe for heating the connector and adhesive bond. A problem with this wire coil and delivery assembly is that it requires the use of laser energy. As a result, the assembly is relatively expensive to manufacture and make available to clinicians.

A further wire coil and delivery device includes a coil with a preprogrammed, helical configuration and a proximal eye for attaching to the distal knuckle of a release wire. To release the wire coil, the release wire knuckle is removed from the eye. A problem with this wire coil and delivery device is that inadvertent lateral movement potentially detaches the eye and knuckle. As a result, the coil is prematurely released in the vascular system of a patient at an undesirable site.

Yet a further wire coil and delivery device comprise a platinum guidewire tip attached to a stainless steel guidewire. To release the platinum guidewire tip, a positive current is applied to the stainless steel guidewire for corroding away the guidewire in the bloodstream and releasing the platinum guidewire tip. A problem with this method of detaching the guidewire tip is that it is relatively time intensive and prolongs the duration of an artificial embolization procedure.

A major problem with all of these devices and procedures is the precise positioning of the occlusion or intravascular treatment device within the vascular system of the patient. Once released, the treatment device is normally irretrievable and very difficult to reposition. What is needed is a delivery system for precise positioning and repositioning of the device once introduced into the vascular system. What is also needed is an intravascular treatment system in which the device can be retrieved and redeployed at another occlusion site should the physician so desire.

SUMMARY OF THE INVENTION

The foregoing problems are solved and a technical advance is achieved in an illustrative intravascular treatment system in which a percutaneous release mechanism is utilized to position an intravascular treatment device. The percutaneous release mechanism includes an inner member having a connection mechanism positioned proximate the distal end thereof with a flexible outer member tube for containing the inner member and connection mechanism in a passage thereof. The intravascular treatment device includes a connection mechanism positioned thereon for interconnecting with the connection mechanism of the inner member. The first and second connection members are interconnected and drawn into the passage of the flexible outer member tube about the distal end thereof. This advantageously permits extension of the treatment device in a delivery state beyond the distal end of an outer guiding catheter for pinpoint positioning of the treatment device in the vascular system of a patient. Should repositioning of the device be required, the percutaneous release mechanism connected to the device readily facilitates repositioning of the treatment device without concern for detachment therefrom. The release mechanism also includes a handle having a first part attached to the inner member and a second part slidably connected thereto and to the flexible outer member tube. Movement of the proximal end of the inner member via the handle is translated to the distal end of the release mechanism to extend the interconnected connection mechanisms from the passage of the flexible outer member tube and to position the treatment device in the treatment state.

The release mechanism further comprises a rigid tube adjacent the distal end of and over the flexible outer member tube which contains a treatment device, such as an occlusion coil, in an delivery state.

The intravascular treatment system of the present invention includes an intravascular treatment device, such as, for example, an occlusion coil or blood filter, including a first connection mechanism and having a delivery state and a treatment state. The system further includes the percutaneous release mechanism comprising an outer member and an inner member positioned in the passage of the outer member. The inner member also has a second connection mechanism positioned proximate the distal end thereof. The interconnected connection mechanisms are interconnected and positioned in the passage of the outer member when the treatment device is in a delivery state. Movement of the proximal end of the inner member is translated to the distal end thereof to position the treatment device in the treatment state.

The intravascular treatment system further comprises a guiding catheter having a hollow passage extending therethrough and sized for positioning the outer member and treatment device therein. In one aspect of the invention, the intravascular treatment device comprises an occlusion coil having a first connection mechanism which includes a spacing between the turns of the coil wider than the normal spacing between the coil turns. The connection mechanism of the inner member includes a ball connected to the distal segment of the inner member for positioning in the wide spacing between the turns of the occlusion coil. The outer member includes a flexible tube and a rigid tube positioned proximate the distal end of and over the flexible tube for containing the occlusion coil therein. The rigid tube is advantageously utilized for loading the occlusion coil and flexible outer member tube into a guiding catheter.

In another aspect of the invention, the treatment device comprises a blood filter wherein the connection mechanisms of the release mechanism and filter comprise first and second wires having recesses formed transversely therein for interlocking each other in the outer member about the distal end thereof. The system further comprises a hollow filter catheter in which the blood filter is positioned in the delivery state.

The outer member of the percutaneous release mechanism comprises an inner cannula of which an outer coil is positioned longitudinally therearound. The inner member of the system comprises an inner stylet wire positioned in the inner cannula and has a distal end attached to one of the connection mechanisms. The outer member further comprises an outer cannula positioned over and attached to the outer coil and in which the interconnected connection mechanisms are selectively positioned therein. The system further comprises a second outer cannula positioned over and attached to the proximal end of the outer coil. An intermediate cannula is positioned in the passage of the second outer cannula, engaging the proximal end of the outer coil and attached to the proximal end of the inner stylet wire. This arrangement advantageously provides for a slim-line handle for detaching the treatment device from the distal end of the release mechanism. To prevent inadvertent release of the treatment device, a peel-away sleeve is fixedly positioned over the second outer cannula and the intermediate cannula, which forms the push-button handle.

BRIEF DESCRIPTION OF THE DRAWING

FIG. 1 depicts an illustrative intravascular treatment system including a percutaneous release mechanism attached to an intravascular treatment device in a delivery state;

FIG. 2 depicts an enlarged, partially sectioned view of the intravascular treatment system of FIG. 1;

FIG. 3 depicts the intravascular treatment system of FIG. 1 with the treatment device in a treatment state;

FIG. 4 depicts an enlarged, partially sectioned end view of the percutaneous release mechanism and treatment device of FIG. 3;

FIG. 7 depicts an enlarged partially sectioned view of the percutaneous release mechanism of FIG. 5; and FIG. 8 depicts an intravascular treatment device such as a vena cava blood filter positioned in a patient blood vessel.

DETAILED DESCRIPTION

Figure 5:
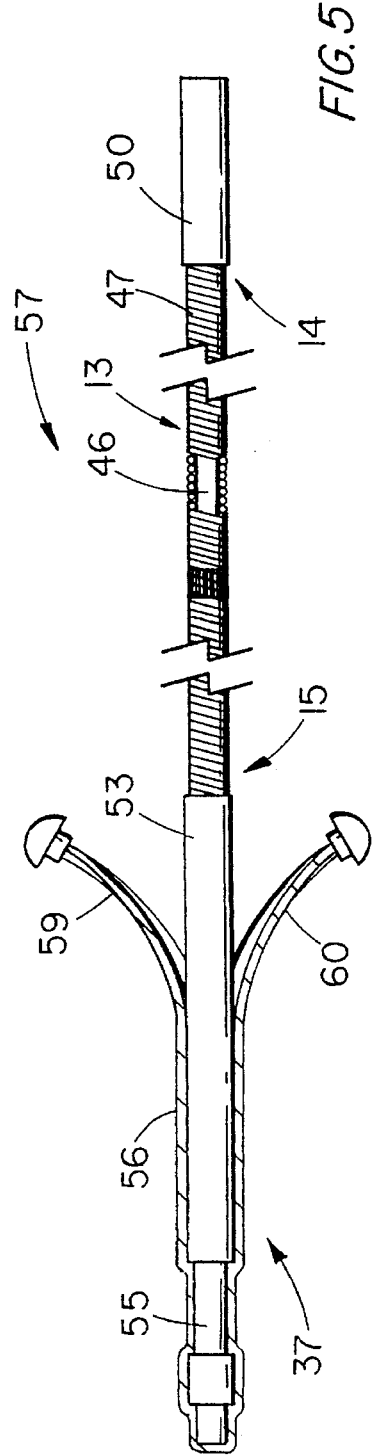
FIG. 5 depicts another aspect of the percutaneous release mechanism of the present invention.

FIG. 1 depicts an illustrative intravascular treatment system 10, which includes percutaneous release mechanism 57 and an intravascular treatment device attached thereto, being introduced into hollow passage 22 of well-known guiding catheter 21. Rigid tube 36 with the intravascular treatment device in a delivery state contained therein is initially positioned proximate distal end 14 of outer member 13, such as flexible, polytetrafluoroethylene tube 35. The treatment device includes a connection mechanism that is interconnected to another connection mechanism positioned proximate the distal end of inner member 17 in the outer flexible member tube. The rigid containment tube is inserted into proximal hub 62 of guiding catheter 21 for loading the interconnected intravascular treatment device and percutaneous release mechanism 57 into hollow passage 22 of the guiding catheter. The treatment device and flexible outer member tube 35 of the release mechanism are urged forward into the passage of the guiding catheter through rigid containment tube 36. After the treatment device and flexible outer member tube have been initially inserted into the guiding catheter, the rigid containment tube can be further retracted proximally over the outer flexible member tube toward distal end 15 thereof.

FIG. 2 depicts an enlarged, partially sectioned view of intravascular treatment system 10 of FIG. 1 and, in particular, distal end 14 of flexible outer member tube 35 positioned within the proximal end of rigid containment tube 36. Intravascular treatment device 11, such as occlusion coil 23 in a delivery state, is positioned and contained within the rigid containment tube. Included at proximal end 25 of occlusion coil 23 is connection mechanism 12 that includes spacing 28 that is wider than normal spacing 27 between turns 26 of the occlusion coil. Positioned proximate distal end 19 of inner member 17 is second connection mechanism 18 that interconnects with connection mechanism 12 of the occlusion coil. Second connection mechanism 18 includes ball 34 that is connected to distal segment 30 of inner member 17. Cross-sectional area 31 of distal segment 30 is smaller than cross-section area 32 of proximal segment 29 of the inner member. Cross-sectional area 33 of ball 34 is larger than the cross-sectional area of distal segment 30. This allows insertion of the ball into spacing 28 of the coil with the remaining distal turns of the coil being trapped between the distal end of the outer flexible member tube and distal segment 30 of the inner member.

To release the occlusion coil from release mechanism 57, the distal end of the release mechanism with the occlusion coil attached thereto is extended from the distal end of the guiding catheter and positioned at the intravascular occlusion site. Connection mechanisms 12 and 18 proximate proximal end 25 of the occlusion coil and distal end 19 of inner member 17 are released, respectively, thereby permanently positioning the occlusion coil at the intravascular occlusion site. The release mechanism and occlusion coil are percutaneously positioned in the vascular system of a patient using well-known radiographic, fluoroscopic, or X-ray equipment.

Occlusion coil 23 depicted in FIG. 2 includes a plurality of turns 26 with normal spacing 27 therebetween. Dacron fibers 58 are positioned in spaces 27 of the coil to further facilitate collection of thrombi and occlusion of the vessel. As previously suggested, second spacing 28 between coil turns 26 comprises second connection mechanism 18 for connecting the coil to inner member 17.

As also depicted in FIG. 2, percutaneous release mechanism 57 for use with intravascular treatment device 11, such as occlusion coil 23, comprises outer member 13, such as flexible, polytetrafluoroethylene tube 35, and inner member 17, such as a stainless steel stylet wire, positioned in passage 16 of the flexible tube. Connection mechanism 18, such as ball 34, is positioned at distal end 19 of the inner member. Flexible tube 35 of outer member 13 includes distal end 14 with rigid, stainless steel containment tube 36 positioned proximate the distal end of and over the flexible tube. The rigid, stainless steel containment tube maintains the occlusion coil in a delivery state when positioned in the hollow passage of the containment tube.

Percutaneous release mechanism 57 depicted in FIG. 1 also includes a push-button handle 37, which basically comprises two parts 38 and 39. Thumb push-button 38 is attached to proximal end 20 of inner member 17, whereas perpendicularly oriented annular disk 39 is slidably connected to thumb push-button 38 and proximal end 15 of the flexible outer member tube. Movement of first and second handle parts 38 and 39 is translated to the distal end of inner member 17 for extension of the connection mechanisms from the passage of the flexible outer member tube and for releasing the occlusion coil at the treatment site.

FIG. 3 depicts intravascular treatment system 10 of FIG. 1 with distal end 14 of flexible outer member tube 35 extending from the distal end of guiding catheter 21 and occlusion coil 23 released therefrom. Occlusion coil 23, which is in a treatment state, is depicted in a tubular configuration with dacron fibers 58 extending radially therefrom for occlusion of a patient's vessel. Distal end 19 of inner member 17 is extended from flexible outer member tube, thereby releasing proximal end 25 of the occlusion coil therefrom. Proximal end 25 of the occlusion coil includes second connection mechanism 18 with wide space 28 between the turns of the coil, whereas distal end 24 of the coil includes turns 26 with normal spacing 27 therebetween.

FIG. 4 depicts an enlarged, partially sectioned end view of percutaneous release mechanism 57 of FIG. 3 with occlusion coil 23 in a treatment state released therefrom. As depicted, distal end 14 of flexible outer member tube 35 is extended through passage 22 of guiding catheter 21 and beyond the distal end thereof. Inner member 17 extends through passage 16 of outer member 13 with second connection mechanism 18 of the inner member extended beyond distal end 14 of flexible outer member tube 35. As previously suggested, inner member 17 includes proximal segment 29 and distal segment 30. Second connection mechanism 18 includes ball 34, which is connected to reduced cross-sectional area 31 of distal segment 30. Proximal end 25 of the occlusion coil including first connection mechanism 12 has been released from second connection mechanism 18 of inner member 17.

FIG. 5 depicts another aspect of percutaneous release mechanism 57 of the present invention. This percutaneous release mechanism is utilized to introduce and release another intravascular treatment device such as a blood filter known as the Gianturco-Roehm BIRD'S NEST vena cava filter and commercially available from Cook Incorporated, Bloomington, Ind. Percutaneous release mechanism 57 includes outer member 13 with push-button handle 37 attached to proximal end 15 of the outer member. Peel-away sleeve 56 with pull tabs 59 and 60 are heat shrunk over handle 37 to prevent inadvertent operation of the handle and premature release of the intravascular treatment device. Outer member 13 comprises inner cannula 46 with outer coil 47 positioned longitudinally therearound. First outer cannula 50 is soldered to the inner cannula and outer coil about distal end 14 of the outer member. Similarly, second outer cannula 53 is soldered to the inner cannula and outer coil proximate proximal end 15 of the outer member. Second outer cannula 53 comprises or extends to the proximal end of the inner cannula and forms one part of handle 37. The second part of push-button handle 37 includes intermediate cannula 55 which is positioned in the passage between inner cannula 46 and outer cannula 53.

Figure 6:
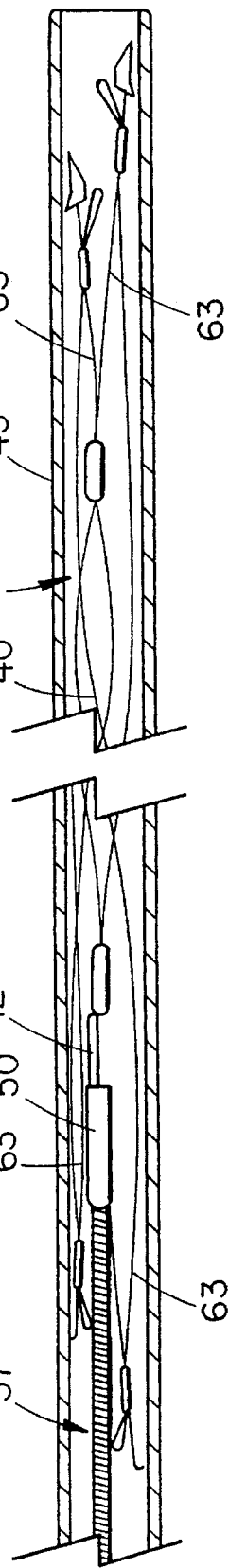
FIG. 6 depicts a partially sectioned view of an intravascular treatment system utilizing the percutaneous release mechanism of FIG. 5.

FIG. 6 depicts a partially sectioned view of intravascular treatment system 10 of the present invention with second aspect release mechanism 57 attached to intravascular treatment device 11 such as vena cava blood filter 40. The release mechanism and treatment device are interconnected and inserted in hollow filter catheter 45 with the blood filter in a delivery state. The blood filter includes a plurality of hook wire struts 63 of which first connection mechanism 12 is attached to one of the struts. The second connection mechanism of release mechanism 57 is contained within first outer cannula 50 and attached to first connection mechanism 12 of the treatment device.

FIG. 7 depicts an enlarged partially sectioned view of percutaneous release mechanism 57 of FIG. 5, which is connected to first wire 42 which is part of first connection mechanism 12 of the treatment device. Inner member 17 of the release mechanism includes inner stylet wire 48 with second connection mechanism wire 41 soldered to distal end 49 of the inner stylet wire. Second connection mechanism wire includes transverse recess channel 43 for engaging and interconnecting first connection mechanism wire 42 of the treatment device. Recessed channel 44 is transversely positioned proximate the proximal end of first wire 42. The interconnected first and second wires engage each other and are maintained in the passage of first outer cannula 50. Proximal end 61 of inner stylet wire 48 extends proximately from the proximal end of inner cannula 46 and is soldered to intermediate cannula 55 and forms one part of push-button handle 37.

Outer member 13 includes inner cannula 46 and outer coil 47 positioned longitudinally therearound to minimize kinking of the inner cannula. Proximal end 51 of first outer cannula 50 is soldered to distal end 52 of outer coil 47 and inner cannula 46. As depicted, turns 64 of outer coil 47 are stretched proximate the proximal end of the coil to form a spring for push-button handle 37. As also shown, very proximal end turns 65 of the coil remain in close contact for engaging intermediate cannula 55. Proximal end 54 of outer coil 47 just distal of stretched turns 64 is soldered to the inner cannula with the distal end of second outer cannula attached thereto. As previously suggested, the distal end of intermediate cannula 55 is inserted in the passage between second outer cannula 53 and inner cannula 46 to engage end turns 65 of the outer coil. The proximal end of the intermediate cannula is soldered to inner stylet wire 48 along with third outer cannula 66, which forms the second part of release mechanism handle 37. To release the treatment device, the second part of the handle is pushed into the passage of second outer cannula 53. The inner stylet wire is urged forward with first and second connection mechanism wires 42 and 41 being extended distally from first outer cannula 50. As a result, wire 42 of the connection mechanism mounted on the treatment device is released from the release mechanism, thereby positioning the treatment device in a treatment state in a vessel of the patient.

FIG. 8 depicts intravascular treatment device 11 such as vena cava blood filter 40 in a delivery state positioned in patient blood vessel 67. Distal end 14 of percutaneous release mechanism 57 is depicted with connection mechanism wire 41 extending therefrom, thereby releasing connection mechanism wire 42 of the blood filter so as to assume the treatment state in patient blood vessel 67. As previously suggested, the BIRD'S NEST vena cava filter is commercially available from Cook Incorporated, Bloomington, Ind., and is more fully described in U.S. Pat. No. 4,494,531 and fully incorporated herein by reference. This blood clot filter is particularly suited for filtering emboli from blood circulating through the inferior vena cava of a human or animal body. After placement of the blood clot filter in the blood vessel of the patient, pull tabs 59 and 60 are pulled to longitudinally split apart peel-away sleeve 56. The peel-away sleeve is maintained around handle 37 of the release mechanism to ensure that the release mechanism is not inadvertently operated and thereby prematurely releasing the blood clot filter therefrom.

While the invention has been illustrated and described in detail in the drawings and foregoing description, the same is to be considered as illustrative and not restrictive in character, it being understood that only the preferred embodiment of a percutaneous release mechanism for use with an intravascular treatment device and an intravascular treatment system has been shown and described and that all changes and modifications that come within the spirit and scope of the invention as defined by the hereinafter claims are desired to be protected. In particular, any intravascular treatment system utilizing a percutaneous release mechanism in combination with an intravascular treatment device is contemplated. Although only preferred embodiments of a percutaneous release mechanism for a vascular occlusion coil and blood filter have been described, it is contemplated that other vascular treatment devices may be utilized in combination with a percutaneous release mechanism suited for the particular treatment device. In further contemplation, the release mechanism includes an outer member of which an inner member is positioned therein and includes a connection mechanism for interconnecting with the connection mechanism of the treatment device. The two interconnection mechanisms are drawn within the distal end of the outer member of the release mechanism to maintain the treatment device in a delivery state in an outer cannula or catheter. The release mechanism along with the treatment device are extended from the distal end of a guiding catheter for placement and subsequent release in the vascular system of a patient. The release mechanism remains connected to the treatment device until the treatment device has been properly positioned. Continued connection to the treatment device allows for selective placement and repositioning of the treatment device by the physician.

What is claimed is:

1. An intravascular treatment system (10) comprising:
   an intravascular treatment device (11) including a first connection mechanism (12) and having a delivery state and a treatment state and
   a percutaneous release mechanism (57) releasably attached to said intravascular treatment device in said delivery state and including:
      an outer member (13) having a distal end (14), a proximal end (15), and a passage (16) extending longitudinally therebetween, said outer member including an inner cannula (46) and outer coil (47) position longitudinally therearound; and
      an inner member (17) positioned in said passage of said outer member, having a second connection mechanism (18) positioned proximate a distal end (19) thereof and a proximal end (20) positioned proximate said proximal end of said outer member, said first and said second connection mechanisms being interconnected and positioned in said passage when said treatment device is in said delivery state, whereby movement of said proximal end of said inner member is translated to said distal end thereof to extend from said passage said first and said second connection mechanisms interconnected in said passage and to release said first and said second connection mechanisms from each other when said treatment device is positioned in said treatment state.

2. The system of claim 1 wherein said first connection mechanism (12) comprises a first wire (42) attached to said treatment device.

3. The system of claim 2 wherein said second connection mechanism (18) comprises a second wire (41) attached to said distal end of said inner member and interlockable with said first wire in said outer member.

4. The system of claim 3 wherein each of said first and said second wires includes a recessed channel (44,43) positioned transversely thereacross in which an end of the other of said first and said second wires is positioned and maintained therein when positioned in said outer member.

5. The system of claim 1 wherein said inner member comprises an inner stylet wire (48) positioned in said inner cannula and having a distal end (49) attached to said second connection mechanism.

6. The system of claim 1 wherein said outer member further comprises a first outer cannula (50) having a proximal end (51) positioned over and attached to a distal end (52) of said outer coil and wherein said second connection mechanism is selectively positioned in said first outer cannula.

7. The system of claim 6 further comprising a second outer cannula (53) positioned over and attached to a proximal end (54) of said outer coil and an intermediate cannula (55) positioned in said second outer cannula engaging said outer coil and attached to a proximal end (61) of said inner stylet wire.

8. The system of claim 7 further comprising a peel-away sleeve (56) fixedly positioned over said second outer cannula and said intermediate cannula.

9. An intravascular treatment system (10) comprising:
   an intravascular blood filter (40) including a first connection mechanism (12) and having a delivery state and a treatment state and
   a percutaneous release mechanism (57) releasably attached to said intravascular blood filter in said delivery state and including:
      an outer member (13) having a distal end (14), a proximal end (15), and a passage (16) extending longitudinally therebetween, said outer member including an inner cannula (46) and an outer coil (47) positioned longitudinally therearound; and
      an inner member (17) positioned in said passage of said outer member, having a second connection mechanism (18) positioned proximate a distal end (19) thereof and a proximal end (20) positioned proximate said proximal end of said outer member, said first and said second connection mechanisms being interconnected and positioned in said passage when said treatment device is in said delivery state, whereby movement of said proximal end of said inner member is translated to said distal end thereof to extend from said passage said first and said second connection mechanisms interconnected in said passage and to release said first and said second connection mechanisms from each other when said treatment device is positioned in said treatment state.

10. The system of claim 9 wherein said first connection mechanism comprises a first wire (42) attached to said blood filter.

11. The system of claim 10 wherein said second connection mechanism comprises a second wire (41) attached to said distal end of said inner member and interlockable with said first wire in said outer member.

12. The system of claim 11 wherein each of said first and said second wires includes a recessed channel (44,43) positioned transversely thereacross in which an end of the other of said first and said second wires is positioned and maintained therein when positioned in said outer member.

13. The system of claim 9 further comprising a hollow catheter (45) in which said intravascular blood filter is positioned in said delivery state.

14. The system of claim 9 wherein said inner member comprises an inner stylet wire (48) positioned in said inner cannula and having a distal end (49) attached to said second connection mechanism.

15. The system of claim 9 wherein said outer member further comprises a first outer cannula (50) having a proximal end (51) positioned over and attached to a distal end (52) of said outer coil and wherein said second connection mechanism is selectively positioned in said first outer cannula.

16. The system of claim 15 further comprising a second outer cannula (53) positioned over and attached to a proximal end (54) of said outer coil and an intermediate cannula (55) positioned in said second outer cannula engaging said outer coil and attached to a proximal end (61) of said inner stylet wire.

17. The system of claim 16 further comprising a peel-away sleeve (56) fixedly positioned over said second outer cannula and said intermediate cannula.

18. An intravascular treatment system (10) comprising:

an intravascular blood filter (40) including a first connection wire (42) and having a delivery state and a treatment state;

a hollow catheter (45) in which said intravascular blood filter is positioned in said delivery state; and a percutaneous release mechanism (57) releasably attached to said intravascular blood filter in said delivery state and including:

an outer member (13) having a distal end (14), a proximal end (15), and a passage (16) extending longitudinally therebetween, said outer member including an inner cannula (46), an outer coil (47) positioned longitudinally therearound, and a first outer cannula (50) having a proximal end (51) positioned over and attached to a distal end (52) of said outer coil;

an inner member (17) including an inner stylet wire (48) positioned in said inner cannula and having a distal end (49) attached to a second connection wire (41) positioned proximate a distal end (19) of said inner member, said inner member also having a proximal end (20) positioned proximate said proximal end of said outer member, said first and said second connection wires being interconnected and positioned in said passage when said blood filter is in said delivery state;

a push-button handle (37) including a second outer cannula (53) positioned over and attached to a proximal end (54) of said outer coil and an intermediate cannula (55) positioned in said second outer cannula and attached to a proximal end (61) of said inner stylet wire; and a peel-away sleeve (56) fixedly positioned over said second cannula and said intermediate cannula, whereby movement of said proximal end of said inner member is translated to said distal end thereof to extend from said passage said first and said second connection wires interconnected in said passage and to release said first and said second connection wires from each other when said blood filter is positioned in said treatment state.

\* \* \* \* \*